United States Patent [19]

Brown

[11] Patent Number: 4,808,589

[45] Date of Patent: Feb. 28, 1989

[54] PYRIMIDONE DERIVATIVES

[75] Inventor: Thomas H. Brown, Tewin, United Kingdom

[73] Assignee: Smith Kline & French Laboratories Limited, Welwyn Garden City, England

[21] Appl. No.: 465,090

[22] Filed: Feb. 9, 1983

[30] Foreign Application Priority Data

Feb. 20, 1982 [GB] United Kingdom ................. 8205075

[51] Int. Cl.$^4$ ................. C07D 401/06; C07D 401/12; A61K 31/505
[52] U.S. Cl. .................................... 514/269; 544/319; 544/321
[58] Field of Search ....................... 544/319, 321, 314; 424/251; 514/269

[56] References Cited

U.S. PATENT DOCUMENTS

| 4,154,834 | 5/1979 | Brown et al. | 424/251 |
|---|---|---|---|
| 4,218,452 | 8/1980 | Brown et al. | 424/251 |
| 4,234,588 | 11/1980 | Brown et al. | 424/251 |
| 4,252,819 | 2/1981 | Hirata et al. | 424/285 |

FOREIGN PATENT DOCUMENTS

| 60730 | 9/1982 | European Pat. Off. . |
|---|---|---|
| 60697 | 9/1982 | European Pat. Off. . |
| 55-115877 | 9/1980 | Japan . |

Primary Examiner—Robert Gerstl
Attorney, Agent, or Firm—Linda E. Hall; Janice E. Williams; Alan D. Lourie

[57] ABSTRACT

This invention provides 5-substituted-4-pyrimidones having in the 2-position a heterocyclic (or substituted phenyl) alkyl group. These compounds have histamine $H_2$-antagonist activity.

29 Claims, No Drawings

PYRIMIDONE DERIVATIVES

This invention relates to pyrimidone compounds having histamine H$_2$-antagonist activity, their preparation, and pharmaceutical compositions containing them.

Histamine, a physiologically active compound endogenous in mammals, exerts its action by interacting with certain sites called receptors. One type of receptor is known as a histamine H$_1$-receptor (Ash and Schild, Brit. J. Pharmac. 1966, 27, 427) and the actions of histamine mediated through these receptors are blocked by drugs commonly called "antihistamines" (histamine H$_1$-antagonists) a common example of which is mepyramine. A second type of histamine receptor is known as the H$_2$-receptor (Black et al, Nature 1972, 236,385). These receptors are not blocked by mepyramine but are blocked by burimamide. Compounds which block these histamine H$_2$-receptors are called histamine H$_2$-antagonists.

Histamine H$_2$-antagonists are useful in treating disease conditions caused by the biological effects of histamine mediated through H$_2$-receptors, for example, as inhibitors of gastric acid secretion, in the treatment of inflammation mediated through histamine H$_2$-receptors and as agents which act on the cardiovascular system, for example, as inhibitors of effects of histamine on blood pressure mediated through histamine H$_2$-receptors.

Cimetidine is an example of a histamine H$_2$-antagonist. Cimetidine has been shown to be useful in the treatment of duodenal, gastric, recurrent and stomal ulceration, and reflux oesophagitis and in the management of patients who are at high risk from hemorrhage of the upper gastrointestinal tract.

In some physiological conditions the biological actions of histamine are mediated through both histamine H$_1$- and H$_2$-receptors and blockade of both types of receptors is useful. These conditions include inflammation mediated by histamine, for example skin inflammation, and those hypersensitivity responses due to the action of histamine at H$_1$- and H$_2$-receptors, for example allergies.

Japanese Patent Application No. 55-115877 discloses and claims histamine H$_2$-antagonist compounds of the formula:

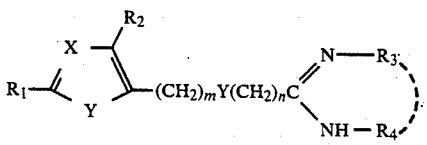

and acid addition salts thereof, where "X is nitrogen or methine (=CH—); Y's are, the same or different, oxygen or sulfur; R$_1$ is hydrogen, lower alkyl, substituted or unsubstituted amino(lower)alkyl or cycloalkylamino(lower) alkyl optionally interrupted with oxygen; R$_2$ is hydrogen or lower alkyl; m and n are each integer of 1 to 3;" and inter alia "R$_3$ and R$_4$ together with the carbon atom and nitrogen atoms bonded thereto may form an optionally substituted 5 or 6 membered heterocyclic group".

A small group of compounds has now been invented having a particularly favourable level of histamine H$_2$antagonist activity. Some of these compounds fall within the broad definition above when the heterocyclic group including R$_3$ and R$_4$ is a pyrimidone group having certain substituents in its 5-position According to the present invention there is provided compounds of formula (I):

or a pharmaceutically acceptable salt thereof, where

W is a 2-furanyl or 2-thienyl group optionally substituted in the 5-position with a group $R^1R^2N(CH_2)_a$—; a 2-pyridyl group optionally substituted in the 4- or 6-position with a group $R^1R^2N(CH_2)_a$—; a phenyl group substituted in the 3- or 4-position with a group $R^1R^2N(CH_2)_a$—; a 4-imidazolyl group optionally substituted in the 5-position with methyl or bromine; a 2-pyridyl group optionally substituted in the 3-position with $C_{1-4}$ alkyl, $C_{1-4}$ alkoxy, halogen, amino or hydroxy; a 2-thiazolyl group or a 2-guanidino-4-thiazolyl group;

X is $(CH_2)_b$ in which b is from 3 to 6, or $(CH_2)_dS(CH_2)_e$ in which d and e are the same or different and are from 1 to 3 or, when W is substituted phenyl or 2-pyridyl substituted in the 4- or 6- position with a group $R^1R^2N(CH_2)_a$—, $O(CH_2)_f$ in which f is from 2 to 5;

Z is hydrogen or $C_{1-4}$ alkyl; A is $C_l$—$C_5$ alkylene or $(CH_2)_pA^1(CH_2)_q$— where $A^1$ is oxygen or sulphur and p and q are such that their sum is from 1 to 4;

B is an optionally substituted pyridyl, where the optional substituent is one or more $C_{1-4}$ alkyl, or $C_{1-4}$ alkoxy or hydroxy groups or halogen atoms or an N-oxo group or a phenyl group optionally substituted with one or more $C_{1-4}$ alkyl or $C_{1-4}$ alkoxy groups or halogen atoms or B is a 6-(2,3-dihydro-1,4-benzodioxinyl) or a 5-(1,3-benzodioxolyl) group or B is a 2-furanyl or 2-thienyl group optionally substituted in the 5-position with a group $R^1R^2N(CH_2)_a$—; a phenyl group substituted in the 3- or 4-position with a group $R^1R^2N(CH_2)_a$— or a 3-pyridyl group substituted in the 5- or 6-position or a 3-pyridyl group substituted in the 2-position by a group $R^1R^2N(CH_2)_a$—;

$R^1$ and $R^2$ can be the same or different and are hydrogen or $C_{1-4}$ alkyl or together form a 1,4-butanediyl, 1,5-pentanediyl, 1,6-hexanediyl or 1,7-heptanediyl group; and a is 1 to 4.

One group of compounds within the scope of this invention is that where W is 2-furanyl or 2-thienyl optionally substituted in the 5-position with $R^1R^2N(CH_2)_a$—; 4-imidazolyl optionally substituted in the 5-position with methyl or bromine; or a 2-pyridyl group substituted in the 4-position with $R^1R^2N(CH_2)_a$—; or phenyl substituted in the 3-position with $R^1R^2N(CH_2)_a$— or 2-pyridyl optionally substituted in the 3-position with $C_{1-4}$ alkyl, $C_{1-4}$ alkoxy, halogen, amino or hydroxy; 2-thiazolyl or 2-guanidino-4-thiazolyl.

Within this group preferably W is a 2-furanyl or 2-thienyl group substituted in the 5-position or a 2-pyridyl group substituted in the 4-position or a phenyl substituted in the 3-position with the group $R^1R^2N(CH_2)_a$—; or is a 2-guanidino-4-thiazolyl group.

Where W is a 2-furanyl or 2-thienyl group substituted in the 5-position with a group $R^1R^2N(CH_2)_a$—, preferably $R^1$ and $R^2$ are both methyl and a is 1.

Of these particular values, W is preferably 5-dimethylaminomethyl-2-furanyl.

Where W is a 2-pyridyl group substituted in the 4-position with a group $R^1R^2N(CH_2)_a$—, preferably $R^1$ and $R^2$ are both methyl or together represent a 1,5-pentanediyl group and a is 1.

Of these values, W is preferably 4-(1-piperidinylmethyl)pyrid-2-yl.

Where W is phenyl substituted in the 3-position with a group $R^1R^2N(CH_2)_a$—, preferably $R^1$ and $R^2$ are both methyl or together represent a 1,5-pentanediyl group and a is 1.

Of these values, W is 3-(1-piperidinylmethyl)phenyl.

In particular, X can be $CH_2SCH_2CH_2$ or $OCH_2CH_2CH_2$.

By way of example, Z can be hydrogen, methyl, ethyl n-propyl or n-butyl but preferably Z is hydrogen.

Examples of $C_{1-5}$ alkylene groups which A represents are methylene, 1,2-ethanediyl, 1,3-propanediyl or 1,4-butanediyl. Examples of groups which A represents when $A^1$ is oxygen, are oxymethyl, methoxymethyl, methoxyethyl, ethoxymethyl and ethoxyethyl. Examples of groups which A represent when $A^1$ is sulphur are methylthiomethyl, methylthioethyl, ethylthiomethyl and ethylthioethyl. Preferably A is methylene.

When B represents hydroxypyridyl and the hydroxy group is in position 2 or 4 relative to the pyridine nitrogen atom, the group exists predominantly as the keto-tautomer. This keto-enol tautomerism can be represented by the partial structures below:

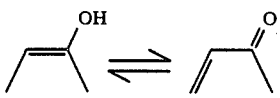

Further, the hydroxypyridine (or pyridone) group has a number of isomeric forms. It is understood that reference to hydroxypyridine or pyridone includes reference to all isomers and tautomers unless the context requires otherwise.

One particular sub-group of compounds within the scope of this invention is that where B is a 6-(2,3-dihydro-1,4-benzodioxinyl) or 5-(1,3-benzodioxolyl) group, an optionally substituted 2-pyridyl, 3-pyridyl, 4-pyridyl, (where the optional substituents are one or more $C_{1-4}$ alkyl or $C_{1-4}$ alkoxy groups), or is a pyridyl group substituted with hydroxy, or is a 2-furanyl or 2-thienyl group substituted in the 5-position or a 2-pyridyl group substituted in the 6-position or a 4-pyridyl group substituted in the 2-position with a group $R^1R^2N(CH_2)_a$—.

Within this sub-group, B is preferably 6-(2,3-dihydro-1,4-benzodioxinyl) 5-(1,3-benzodioxolyl), 3-pyridyl, 6-methyl-3-pyridyl, 4,6-dimethyl-3-pyridyl, 5,6-dimethyl-3-pyridyl, 6-methoxy-3-pyridyl, 2-methoxy-4-pyridyl, 6-hydroxy-3-pyridyl, 2-hydroxy-4-pyridyl, 5-dimethylaminomethyl-2-furanyl, or 6-dimethylaminomethyl-3-pyridyl and in particular it is 6-methyl-3-pyridyl or 2-hydroxy-4-pyridyl.

Examples of particular compounds of the invention are:

2-[2-(2-guanidino-4-thiazolylmethylthio)ethyl]-5-(6-methyl-3-pyridylmethyl)-4-pyrimidone, 2-[2-(5-dimethylaminomethyl-2-furanylmethylthio)ethyl]-5-(6-methyl-3-pyridylmethyl)-4-pyrimidone, 2-[3-(5-methyl-4-imidazolylmethylthio)propyl]-5-(6-methyl-3-pyridylmethyl)-4-pyrimidone, 2-[3-(5-dimethylaminomethyl-2-furanylmethylthio)-propyl]-5-(6-methyl-3-pyridylmethyl)-4-pyrimidone, 2-[3-[4-(1-piperidinylmethyl)-2-pyridyloxy]-propyl ]-5-(6-methyl-3-pyridylmethyl)-4-pyrimidone, 2-[3-(4-dimethylaminomethyl-2-pyridylmethylthio)-propyl]-5-(6-methyl-3-pyridylmethyl)-4-pyrimidone, 2-[2-(4-dimethylaminomethyl-2-pyridylmethylthio)ethyl]-5-(6-methyl-3-pyridylmethyl)-4-pyrimidone 2-[3-[3-(1-piperidinylmethyl)-2-phenyloxy]propyl ]-5-(6- methyl-3-pyridylmethyl)-4-pyrimidone 2-[3-[3-(1-piperidinylmethyl)-2-phenyloxy]propyl ]-5-(6-methyl-3-pyridylmethyl)-4-pyrimidone 2-[3-[3-(1-piperidinylmethyl)-2-phenyloxy]propyl ]-5-(2-methoxy-4-pyridylmethyl)-4-pyrimidone (2-hydroxy-4-pyridylmethyl)-4-pyrimidone and their pharmaceutically acceptable salts.

The compounds of formula (I) form addition salts with pharmaceutically acceptable salt-forming acids. Examples of such acids are a hydrochloric, hydrobromic, sulphuric, phosphoric, acetic, citric and maleic acids.

The compounds of formula (I) are shown and described as 4-pyrimidone derivatives and these derivatives exist in equilibrium with the corresponding 6-one tautomers. These compounds also exist to a lesser extent as the hydroxy tautomers.

The compounds of the invention can be prepared by a process which comprises reacting a compound of formula (II):

where W and X are as defined with reference to formula (I) with a compound of formula (III):

where
R is an ester forming group;
A and Z are as defined with reference to formula (I) and $B^1$ is a group B provided that any hydroxy or primary or secondary amino groups in B are protected or any amino group in B is replaced with a chemical precursor, where W and/or B in the product so obtained is 2-thienyl or 2-furanyl, optionally reacting it with a Mannich reagent capable of introducing the group $R^1R^2N(CH_2)_a$- where $R^1$ and $R^2$ are as previously defined provided that neither $R^1$ nor $R^2$ in the product are hydrogen, and a is 1, thereafter removing any protecting groups, converting any chemical precursor for the amino group into amino, where B contains a $C_{1-4}$ alkoxy substituent optionally converting the substituent into hydroxy and optionally thereafter converting a compound of formula (I) so obtained into a salt.

In formula (III) the ester-forming group R can be a $C_{1-4}$ alkyl group and is preferably methyl or ethyl.

In $B^1$, examples of protecting groups for amino are $C_{1-4}$ alkanoyl in particular acetyl. By a chemical precursor for an amino group is meant a group which is not a derivative of an amino group but which can be converted into amino. An example of a chemical precursor for amino in the group $B^1$ is nitro. When B in the compound of formula (I) has a free hydroxy group it is preferably prepared by dealkylating the corresponding $C_{1-4}$ alkoxy (particularly the methoxy) compound.

The reaction between the compounds of formula (II) and (III) is carried out in the presence of base. Examples of suitable bases include alkali metal hydroxides and $C_{1-4}$ alkoxides, sodium hydride, and quaternary ammonium hydroxides, for example benzyltrimethylammonium hydroxide. Preferably the base is sodium ethoxide or sodium methoxide. The reaction can be carried out in the presence of a solvent the choice of which is not critical to the success of the process provided that it is substantially inert to the reagents and product. Preferably the solvent is a $C_{1-4}$ alkanol, (for example, methanol, ethanol or propanol) or dimethylformamide. The reaction can be carried out at moderate temperatures, for example from room temperature to the reflux temperature of the solvent.

The optional step of reacting with a Mannich reagent is an example of the Mannich Reaction and can be carried out under conditions generally used for this type of reaction.

Mannich reagents can be prepared in situ from an amine $R^1R^2NH$ where $R^1$ and $R^2$ are as defined with reference to formula (I) provided that neither $R^1$ nor $R^2$ are hydrogen, and formaldehyde. Alternatively the mannich reagent can be preformed e.g. from a di($C_{1-4}$ alkyl) methylene ammonium salt particularly dimethylmethylene ammonium chloride or iodide or a bis-(di $C_{1-4}$ alkylamino)methane, in particular bis(dimethylamino)methane.

Acid addition salts of compounds of formula (I) can conveniently be formed from the corresponding bases by standard procedures for example by reacting the base with an acid in a $C_{1-4}$ alkanol or by the use of ion exchange resins to form the required salt. Salts of compounds of formula (I) can also be interconverted using an ion exchange resin.

Compounds of formula (II) can be prepared by reacting a compound of formula (IV):

$$WXC\underset{OR^1}{\overset{NH}{\diagup\hspace{-0.5em}\diagdown}} \qquad (IV)$$

where W and X are as defined with reference to formula (I) and $R^1$ is a $C_{1-4}$ alkyl group in particular methyl, with ammonia or an ammonium salt (for example a halide and particularly the chloride) in the presence of a polar organic solvent, for example a $C_{1-4}$ alkanol, in particular methanol, at low to moderate temperatures, for example from 0° C. to the reflux temperature of the solvent and in particular at room temperature.

Compounds of formula (IV) can be prepared by reacting the corresponding nitrile of formula (V):

$$WXCN \qquad (V)$$

with the corresponding $C_{1-4}$ alkanol under acidic conditions. In particular the alkanol is methanol and the acid is hydrochloric acid.

Compounds of formula (V) where X is $(CH_2)_dS(CH_2)_e$ can be prepared by reacting the corresponding halo-nitrile of formula (VI):

$$Hal(CH_2)_eCN \qquad (VI)$$

where e is as defined with reference to formula (I) and Hal is chlorine, bromine or iodine and is particularly chlorine, with a compound of formula (VII):

$$W(CH_2)_dSH \qquad (VII)$$

which can be formed in situ from the corresponding isothiourea (VIIa):

$$W(CH_2)_dSC\underset{NH_2}{\overset{NH}{\diagup\hspace{-0.5em}\diagdown}} \qquad (VIIa)$$

(or salt thereof, particularly the hydrochloride) where W and d are as defined with reference to formula (I) in the presence of base, for example aqueous sodium hydroxide solution.

Compounds of formula (VIIa) can in turn be prepared by reacting a compound of formula (VIII):

$$W(CH_2)_dHal \qquad (VIII)$$

where W is as defined with reference to formula (I) and Hal is chlorine, bromine or iodine (and particularly chlorine) with thiourea.

Compounds of formula (VIII) where d is greater than 1 can be prepared by classical carbon chain extension of compounds of formula (VIII) where d is 1. The halo compound (VIII) where d is 1, is converted to the corresponding nitrile (IX):

$$WCH_2CN \qquad (IX)$$

which is in turn alkanolised to an ester (X):

$$WCH_2CO_2R \qquad (X)$$

where R is a $C_{1-4}$ alkanol. The ester can then be reduced to the corresponding alcohol (XI):

$$WCH_2CH_2OH \qquad (XI)$$

(by using for example lithium aluminium hydride) which can in turn be converted via the corresponding halo compound (XII):

$$WCH_2CH_2Hal \qquad (XII)$$

Compounds of formula (V) where W is phenyl substituted in the 3- or 4-position with a group $R^1R^2N(CH_2)_a$— where $R^1$, $R^2$ and a are as defined with reference to formula (I) where a is 1 and X is $(CH_2)_b$ where b is 3 or where X is $O(CH_2)_f$ where f is 2 are described in Belgian Patent No. 867,106. Compounds of this class where b is greater than 3 and f is greater than 2 can be prepared by analogy with the processes described in these patents or by classical chain extension of the corresponding compound where b is 3 and f is 2 respectively as described above.

Compounds of formula (V) where W is 2-pyridyl substituted in the 4-position with the group $R^1R^2N(CH_2)_a$—where $R^1$, $R^2$ and a are as defined with reference to formula (I) and X is $(CH_2)_b$ where b is 3 and X is $-O(CH_2)_f$ where f is 2 are disclosed in European patent application No 0049173. Compounds of this class where b is greater than 3 and f is greater than 2 respectively can be prepared by analogy with the processes described in these patents or by classical chain extension of the compounds where b is 3 and f is 2. Compounds of formula (V) where W is 2-pyridyl substituted in the 6-position with the group $R^1R^2N(CH_2)_a$—where $R^1$, $R^2$ and a are as defined with reference to formula (I), X is $(CH_2)_b$ or $(CH_2)_f$ where b and f are as defined with reference to formula (I) can be made in an analogous way.

The preparation of compounds of formula (IV) particularly where W is a 5-methyl-4-imidazolyl-, 2-pyridyl, 2-furanyl or 2-thienyl group optionally substituted in the 5-position with a group $R^1R^2N(CH_2)_a$—and X is $(CH_2)_dS(CH_2)_e$ where d and e are as defined with reference to formula (I) is also disclosed in UK patent application No. 2003471A. The preparation of compounds of formula (IV) where W is 2-guanidino-4-thiazolyl is disclosed in UK patent application No. 2052478A.

Compounds of formula (VI) and (VII) are known or can be made by analogy with known methods.

Compounds of formula (III) are known or can be prepared by analogy with known methods for example as described in U.S. Pat. No. 4,234,588 and European patent application No. 0068833.

The activity of the compounds of formula (I) as histamine $H_2$-antagonists can be demonstrated by the inhibition of histamine-stimulated secretion of gastric acid from the lumen-perfused stomachs of rats anaesthetised with urethane. This procedure is referred to in Ash and Schild, Brit. J. Pharmac. Chemother., 27, 427 (1966). The compounds of Examples 1 and 2 hereafter caused 50% inhibition of maximal acid secretion at doses of less than 1 micromole $kg^{-1}$ i.v. Their activity as histamine $H_2$-antagonists can also be demonstrated by their ability to inhibit other actions of histamine which, according to the above mentioned paper of Ash and Schild, are not mediated by histamine $H_1$-receptors. For example, they inhibit the actions of histamine on the isolated guinea pig atrium. The potency of these compounds is illustrated by the effective dose producing 50% inhibition of the histamine-induced tachycardia in the isolated guinea pig atrium (less than $10^{-6}$ Molar).

In order to use a compound of formula (I) or a pharmaceutically acceptable salt thereof for medical purposes, it is normally formulated in accordance with standard pharmaceutical practice as a pharmaceutical composition.

The invention further provides pharmaceutical compositions comprising a compound of formula (I) above or a pharmaceutically acceptable acid addition salt thereof together with a pharmaceutically acceptable carrier.

Compounds of formula (I) and their pharmaceutically acceptable acid addition salts may be administered orally, parenterally, cutaneously or rectally.

Compounds of formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, lactose and sucrose.

Typical parenteral compositions consist of a solution or suspension of the compound or salt in a sterile aqueous carrier or parenterally acceptable oil.

Typical compositions for administration to the skin include lotions and creams in which the compound of formula (I) or a salt thereof is dispersed in a liquid vehicle.

A typical suppository formulation comprises a compound of formula (I) or a pharmaceutically acceptable salt thereof which is active when administered in this way, with a binding and/or lubricating agent for example gelatin or cocoa-butter or other low melting vegetable waxes or fats.

Preferably the composition is in unit dose form for example a tablet or capsule.

Each dosage unit for oral administration contains preferably from 15 to 250 mg (and for parenteral administration contains preferably from 1.5 to 25 mg) of a compound of formula (I) or a pharmaceutically acceptable acid addition salt thereof calculated as the free base.

This invention also provides a method of blocking histamine $H_2$-receptors which comprises administering to an animal an effective amount to block said receptors of a compound of formula (I) or a pharmaceutically acceptable acid addition salt thereof.

The daily dosage regimen for an adult patient is an oral dose between 15 mg and 1500 mg and preferably between 20 mg and 250 mg or an intravenous, subcutaneous or intra-muscular dose of between 1.5 mg and 150 mg and preferably between 5 mg and 20 mg of compound of formula (I) or pharmaceutically acceptable salt thereof calculated as the free base, the composition being administered 1 to 6 imes per day.

The pharmaceutical compositions of the invention will normally be administered for the treatment of gastric and duodenal ulcers and other conditions caused or exacerbated by gastric acidity in the same general manner as that employed for known histamine $H_2$-antagonist, due allowance being made in terms of dose levels for the potency of the compounds of the present invention relative to known histamine $H_2$-antagonist drugs.

The following Examples illustrate the invention.

EXAMPLES

Example 1

(a) 2-Guanidino-4-chloromethylthiazole hydrochloride (5.68 g) was added to a refluxing solution of thiourea (1.90 g) in ethanol (50 ml). The solution was refluxed for five hours. After cooling the solid was filtered off, washed with ethanol and dried. Re-crystallisation from ethanol-methanol gave 5-(2-guanidino-4-thiazolylmethyl)isothiourea dihydrochloride, (6.93 g), m.p. 189°–191.5° C.

(b) To a stirred solution of 5-(2-guanidino-4-thiazolylmethyl)isothiourea dihydrochloride (16.05 g) in water (75 ml) and ethanol (55 ml) under nitrogen was added 3-chloropropionitrile (5.21 g). The solution was cooled to 5° C. and a solution of sodium hydroxide (6.5 g) in water (65 ml) was added, keeping the temperature at 5°–8° C. Solid came out of solution. The mixture was stirred for 1 hour at 0°–10° C. and then slowly allowed to reach room temperature. The solution was extracted with chloroform containing 25% ethanol and the combined organic extracts washed with water (15 ml). After azeotroping to dryness with n-propanol the residue was crystallised from acetone/b 40–60 petroleum ether to give 3-(2-guanidino-4-thiazolylmethylthio)propionitrile as buff crystals (11.47 g), m.p. 126°–129° C.

(c) 3-(2-Guanidino-4-thiazolylmethylthio)propionitrile (12.82 g) was dissolved in a mixture of dry methanol (75 ml) and dry chloroform (150 ml) and the stirred solution was cooled (under nitrogen) in an ice-salt bath to 2° C. Hydrogen chloride gas (dried) was passed through the solution for three hours, keeping the temperature at 0°–10° C. The solution was then allowed to stand in a stoppered flask at ca 0° C. for 20 hours. The solvents were removed at reduced pressure and the oily residue added to ice-water (200 ml) containing potassium carbonate (30 g). The mixture was extracted with chloroform containing 20% methanol (4×150 ml) and the combined organic extracts were dried (MgSO$_4$). The solvent was removed to give methyl 3-(2-guanidino-4thiazolylmethylthio)propionimidate (13.60 g) as a tacky light-brown oil.

(d) Methyl 3-(2-guanidino-4-thiazolylmethylthio)propionimidate (4.09 g), ammonium chloride (0.8 g) and ethanol (25 ml) were stirred at room temperature for 5 hours. The methanol was evaporated at reduced pressure and the residue was chromatographed on silica gel using a chloroform/methanol gradient elution. Fractions containing the main product (as shown by T.L.C.) were combined and the solvent evaporated at reduced pressure. The residue was treated with ethanol containing hydrochloric acid. Excess of solvent was evaporated at reduced pressure and the residue was crystallised from isopropanol to give 3-(2-guanidino-4-thiazolylmethylthio)propionamidine dihydrochloride, (1.63 g) m.p. 174.5°–176.5° C.

(e) Sodium (0.40 g) was dissolved in methanol (15 ml) and 3-(2-guanidino-4-thiazolylmethylthio) propioniamidine dihydrochloride (1.60 g) was added to the solution and the resulting mixture refluxed for 45 minutes. Ethyl 2-formyl-3-(6-methyl-3-pyridyl) propionate (1.07 g) was added portionwise over 5 minutes and the mixture stirred under reflux for 23 hours. After cooling, the mixture was filtered through diatomaceous earth and evaporated to dryness at reduced pressure, and the residue dissolved in water (25 ml). The aqueous solution was extracted with chloroform (3×15 ml) and the combined chloroform extracts washed with water. The combined aqueous extracts were adjusted to pH6 with glacial acetic acid to precipitate a tacky oil which solidified on ice-cooling and was crystallised from isopropanol-methanol to give 2-[2-(2-guanidino-4-thiazolylmethylthio)ethyl]-5-(6-methyl-3-pyridylmethyl)-4-pyrimidone as a light-buff solid (0.95 g), m.p. 210°–215° C.

This solid was purified by dissolving in dilute hydrochloric acid, evaporating the solution to dryness and crystallising the residue from ethanol to give 2-[2-(2-guanidino-4-thiazolylmethylthio)ethyl]-5-(6-methyl-3-pyridylmethyl)-4-pyrimidone trihydrochloride hydrate. m.p. 218°–222° C.

Example 2

(a) Ethyl 3-(5-dimethylaminomethyl-2-furanylmethylthio)propionimidate (27.72 g), ammonium chloride (5.48 g) and ethanol (170 ml) were stirred at room temperature for one hour and then allowed to stand overnight. The ethanol was evaporated at reduced pressure and the residue purified by chromatography on silica gel at medium pressure using chloroform-methanol as eluant. The fractions containing the major product were combined, evaporated to dryness at reduced pressure and treated with ethanol containing anhydrous hydrogen chloride. The solvent was evaporated at reduced pressure to give 3-(5-dimethylaminomethyl-2-furanylmethylthio)propionamidine dihydrochloride (15.65 g).

(b) 3-(5-dimethylaminomethyl-2-furanylmethylthio)propionamidine dihydrochloride (2.36 g) in methanol (10 ml) was added at room temperature to a solution of sodium (0.6 g) in methanol (15 ml). The mixture was heated at reflux temperature for 45 minutes. Ethyl 2-formyl-3-(6-methyl-3-pyridyl)propionate (1.66 g) was added portionwise over 10 minutes and the resulting mixture was heated at reflux temperature for 19 hours. The reaction mixture was cooled, filtered through diatomaceous earth and evaporated to dryness at reduced pressure. The residue was dissolved in diluted aqueous acetic acid and the acidic solution made alkaline with potassium carbonate solution to pH 9, whereupon a white solid precipitated. After leaving the mixture to stand at ca 4° C. for ca 16 hours this solid was collected, washed with water, dried and crystallised from isopropanol-methanol to give 2-[2-(5-dimethylaminomethyl- 2-furanylmethylthio)ethyl]-5-(6-methyl-3-pyridylmethyl)-4-pyrimidone (0.97 g), m.p. 161.5°–162.5° C.

Example 3

(a) Sodium (5.0 g) was dissolved in ethanol (300 ml) and 5-methyl-4-(mercaptomethyl)imidazole (17 g) added, followed by a solution of 4-bromobutyronitrile (16 g) in ethanol (50 ml). The mixture was stirred under reflux for 45 minutes, cooled, filtered and the filtrate evaporated to dryness. The residue was taken up in water and extracted with ethyl acetate. The extract was dried (MgSO$_4$) and solvent removed. Recrystallisation of the product from ethanol-ether gave 4-(5-methyl-4-imidazolylmethylthio)butyronitrile as its hydrochloride salt (12 g).

(b) 4-(5-Methyl-4-imidazolylmethylthio)butyrontrile hydrochloride (1.71 g) was dissolved in a mixture of dry methanol (9 ml) and dry chloroform (18 ml) and the stirred solution cooled under nitrogen to −3° C. (icesalt bath). Dry hydrogen chloride gas was passed through the solution for 1.5 hours, keeping the temperature below 5° C., then allowed to stand in a stoppered flask at ca. 0° C. for 20 hours. The reaction mixture was added to a solution of potassium carbonate (10 g) in water (50 ml), and the mixture so obtained extracted with chloroform (4×20 ml). The combined extracts were dried (K$_2$CO$_3$) and solvent removed to give methyl 4-(5-methyl-4-imidazolylmethyl thio)butyronimidate (1.54 g) as a light-brown oil.

(c) Methyl 4-(5-methyl-4-imidazolylmethylthio)butyronimidate (1.54 g), ammonium chloride (0.36 g) and ethanol (12 ml) were stirred at room temperature for 8 hours. Ethanol was evaporated at reduced pressure and the residue chromatographed on silica gel using a chloroform-methanol gradient elution. Fractions containing the product (as shown by TLC) were combined and solvent removed at reduced pressure to give 4-(5-methyl-4-imidazolylmethylthio)butyronamidine (0.94 g) as a tacky oil.

(d) A solution of 4-(5-methyl-4-imidazolylmethylthio)butyronamidine (0.94 g) in methanol (12 ml) was added to a solution of sodium (0.20 g) in methanol (8 ml) and the resulting mixture refluxed for 0.5 hour. Ethyl 2-formyl-3-(6-methyl-3-pyridyl)propionate (0.84 g) was added portionwise, and the mixture stirred under reflux for 24 hours. Ethanol was evaporated at reduced pressure and the residue dissolved in water (30 ml). Glacial acetic acid was added to pH 7, whereupon a tacky solid precipitated. The supernatant solution was decanted off and the solid was washed with water. The washed solid was then dissolved in dilute ethanolic hydrogen chloride. Excess of solvent was evaporated at reduced pressure and the residue recrystallised from ethanol to give 2-[3-(5-methyl-4-imidazolylmethylthio)propyl]-5-(6-methyl-3-pyridylmethyl)-4-pyrimidone trihydrochloride hydrate (0.66 g), m.p. 167°–170° C.

Example 4

(a) A solution of sodium hydroxide (12.7 g) in water (50 ml) and ethanol (50 ml) was added dropwise over 30 minutes to a solution of furanylmethyl mercaptan (34.25 g) and 4-chlorobutyronitrile (31.58 g) in ethanol (150 ml) under nitrogen at 10° C. (ice-bath). The temperature rose slightly (to 18° C.) and the solution went cloudy. It was stirred at room temperature for 6.5 hours and allowed to stand for 20 hours. Ethanol was removed by evaporation at reduced pressure. The residue was dissolved in water (100 ml) and the solution was extracted with chloroform. The combined extracts were washed with water, dried ($MgSO_4$) and chloroform evaporated at reduced pressure. The residual light-brown liquid was vacuum-distilled to give 4-(2-furanylmethylthio)-butyronitrile (51.16 g), b.p.$_{0.05 \, mm}$112°–5° C.

(b) 4-(2-Furanylmethylthio)butyronitrile (51.09 g), dimethylamine hydrochloride (45.96 g), paraformaldehyde (19.70 g) and ethanol (700 ml) were stirred under reflux for 24 hours. More dimethylaxmine hydrochloride (45.96 g) and paraformaldehyde (19.70 g) were added and the mixture stirred under reflux for another 24 hours. Ethanol was evaporated at reduced pressure and the residue dissolved in water (300 ml). The solution was washed with chloroform (2×150 ml), adjusted to pH 9 with potassium carbonate and extracted with ethyl acetate (3×200 ml). The combined extracts were dried ($K_2CO_3$) and ethyl acetate evaporated at reduced pressure to give a light-brown liquid. The liquid was vacuum-distilled to give 4-(5-dimethylaminomethyl-2-furanylmethylthio)butyronitrile (53.19 g), b.p.$_{0.03 \, mm}$137°–140° C.

(c) 4-(5-Dimethylaminomethyl-2-furanylmethylthio)-butyronitrile (53.13 g) was dissolved in a mixture of dry ethanol (14 ml) and dry chloroform (150 ml), and the stirred solution cooled under nitrogen to 0° C. (ice-salt bath). Dry hydrogen chloride gas was passed through the solution for 2 hours, keeping the temperature at 0°–5° C. The solution was allowed to stand in a stoppered flask at ca. 0°C. This solution was then poured into a solution of potassium carbonate (62 g) in ice-water (ca. 400 ml), the chloroform layer was separated off and the aqueous layer extracted with chloroform (4×200 ml). The combined extracts were dried ($K_2CO_3$) and chloroform removed at reduced pressure to give ethyl 4-(5-dimethylaminomethyl-2-furanylmethylthio)butyronimidate (45.45 g) as a light-brown oil.

(d) Ethyl 4-(5-dimethylaminomethyl-2-furanylmethylthio)butyronimidate (45.45 g), ammonium chloride (8.55 g) and ethanol (260 ml) were stirred at room temperature for 8 hours. Ethanol was evaporated at reduced pressure and the residue chromatographed using silica gel and a chloroform-methanol gradient elution. Fractions containing the required product (as shown by TLC) were combined and solvent evaporated at reduced pressure The residue was treated with dilute ethanolic hydrogen chloride, and excess of solvent evaporated at reduced pressure to give 4-(5-dimethylaminomethyl-2-furanylmethylthio)butyronamidine dihydrochloride (13.59 g) as an oil.

(e) A solution of 4-(5-dimethylaminomethyl-2-furanylmethylthio)butyronamidine dihydrochloride (6.10 g) in methanol (40 ml) was added to a solution of sodium (1.50 g) in methanol (30 ml) and the resulting mixture stirred for 0.5 hour under reflux. Ethyl 2-formyl-3-(6-methyl-3-pyridyl)propionate (4.11 g) was added portionwise over 15 minutes, and the mixture stirred under reflux for 18 hours. After cooling, the mixture was filtered through diatomaceous earth and evaporated to dryness at reduced pressure. The residue was dissolved in water (40 ml) and the aqueous solution was extracted with ether (3×25 ml). The combined ether extracts were then washed with water. The aqueous extracts were combined and adjusted to pH 9 with glacial acetic acid, and a tacky oil precipitated. The mixture was extracted with ethyl acetate (5×30 ml), and the combined extracts washed with water, dried ($MgSO_4$) and ethyl acetate evaporated at reduced pressure. The residue was dissolved in dilute ethanolic hydrogen chloride. Excess of solvent was removed at reduced pressure and the residue dissolved in methanol and decolourised with charcoal. Recrystallisation from ethanol gave 2-[3-(5-dimethylaminomethyl-2-furanylmethylthio)propyl]-5-(6-methyl-3-pyridylmethyl)-4-pyrimidone trihydrochloride hydrate (0.51 g), m.p. 144°–8° C.

Example 5

(a) 2-Bromo-4-methylpyridine (86.02 g), N-bromosuccinimide (97.90 g), benzoyl peroxide (6.6 g) and carbon tetrachloride (1.0 l) were stirred under reflux for 17 hours. The mixture was cooled, filtered and evaporated at reduced pressure to ca. 300 ml. The organic solution was washed in turn with 300 ml. of each of 4% aqueous sodium hydroxide, water and 2% hydrobromic acid. Ether (200 ml) was added to the organic solution and the ethereal solution was dried ($MgSO_4$).

The ethereal solution was stirred at 0° C. (ice-salt bath) and piperidine (94.71 g) added dropwise over 1.25 hours, keeping the temperature below 5° C. Solid formed, and the mixture was stirred at 0°–10° C. for 2 hours, then allowed to stand for 20 hours. The mixture was washed with water (2×200 ml) and the combined aqueous extracts back-washed with ether (150 ml). The combined organic layers were evaporated to dryness under reduced pressure and ether (ca. 200 ml) added to the residue. The solution was filtered and evaporated to dryness under reduced pressure. Water was added to the residue and adjusted to pH 5 with glacial acetic acid. The mixture was extracted with ether and the combined ether extracts washed with water. The aqueous solution was adjusted to pH 9 with sodium carbonate, and extracted with ether (4×200 ml). The combined ether extracts were dried ($MgSO_4$) and ether evaporated at reduced pressure to give 2-bromo-4-(1-piperidinylmethyl)pyridine (43.79 g) as a light-brown oil.

(b) 4-Hydroxybutyronitrile (12.41 g) was added to a suspension of sodium hydride (4.20 g) in dry tetrahydrofuran (160 ml) and the mixture refluxed for 0.5 hour, cooled. To this was added a solution of 2-bromo-4-(1-piperidinylmethyl)pyridine (24.81 g) in dry tetrahydrofuran (40 ml) over 5 minutes, and the mixture refluxed for 24 hours. Tetrahydrofuran was evaporated at reduced pressure, and the residue dissolved in water (ca. 300 ml) and adjusted to pH 4 with hydrochloric acid. The aqueous solution was extracted with methylene chloride (2×50 ml) then adjusted to pH 13 with 2N sodium hydroxide. The aqueous solution was extracted with methylene chloride (4×100 ml), the combined extracts dried (MgSO$_4$) and methylene chloride evaporated at reduced pressure to give 4-[4-(1-piperidinylmethyl)-2-pyridyloxy]butyronitrile (20.45 g).

(c) 4-[4-(1-Piperidinylmethyl)-2-pyridyloxy]butyronitrile (18.45 g) was dissolved in a mixture of dry methanol (80 ml) and dry chloroform (180 ml) and the stirred solution cooled under nitrogen to 0° C. (ice-salt bath). Dry hydrogen chloride gas was passed through the solution for 3 hours, keeping the temperature below 3° C. After having been allowed to stand in a stoppered flask at ca. 4° C. for 24 hours, the solution was added to a solution of potassium carbonate (90 g) in water (400 ml). The chloroform layer was separated off and the aqueous layer extracted with chloroform (3×100 ml). The combined extracts were dried and chloroform removed at reduced pressure to give methyl 4-[4-(1-piperidinylmethyl)-2-pyridyloxy]butyronimidate (20.48 g) as an orange oil.

(d) Methyl 4-[4-(1-piperidinylmethyl)-2-pyridyloxy]butyronimidate (16.68 g), ammonium chloride (3.06 g) and ethanol (100 ml) were stirred at room temperature for 8 hours. Ethanol was evaporated at reduced pressure and the residue chromatographed using silica gel and a chloroform-methanol gradient elution. Fractions containing the required product (as shown by TLC) were combined and solvent evaporated at reduced pressure to give 4-[4-(1-piperidinylmethyl)-2-pyridyloxy]butyronamidine (6.79 g).

(e) A solution of 4-[4-(1-piperidinylmethyl)-2-pyridyloxy]butyronamidine (2.35 g) in methanol (25 ml) was added to a solution of sodium (0.40 g) in methanol (15 ml). The mixture was refluxed for 0.5 hour, and then ethyl 2-formyl-3-(6-methyl-3-pyridyl)propionate (1.66 g) was added portionwise over 10 minutes. The mixture so obtained was refluxed for 20 hours and methanol evaporated at reduced pressure. The residue was dissolved in water (25 ml) and the solution was washed with ether (3–20 ml). The pH of the aqueous solution was carefully adjusted to pH 9 with glacial acetic acid, whereupon a tacky solid precipitated. The supernatant solution was decanted off, and the residue was washed with water and recrystallised from isopropanol-ether to give 2-[[3-[4-(1-piperidinylmethyl)-2-pyridyloxy]propyl]]-5-(6-methyl-3-pyridylmethyl)-4-pyrimidone (0.47 g), m.p. 99°–100° C.

Example 6

(a) 2-Chloromethyl-4-(dimethylaminomethyl)pyridine dihydrochloride (14.67 g) was added to a refluxing solution of thiourea (4.34 g) in ethanol (120 ml) and the solution refluxed for 3 hours, whereupon solid precipitated. After cooling the mixture (ice bath), the solid was filtered and recrystallised from methanol-ethanol to give S-(4-dimethylaminomethyl-2-pyridylmethyl)isothiourea trihydrochloride (11.88 g), m.p. 175°–9° C.

(b) To a solution of S-(4-dimethylaminomethyl-2-pyridylmethyl)isothiourea trihydrochloride (11.88 g) and 4-chlorobutyronitrile (5.21 g) in water (50 ml) and ethanol (35 ml) at 0° C. (ice-salt bath) under nitrogen, was added dropwise over 20 minutes a solution of sodium hydroxide (6.4 g) in water (65 ml), keeping the temperature below 5° C. After having been stirred for 5 hours and allowed to stand for 20 hours, the solution was extracted with 3:1 chloroform:ethanol (3×100 ml) and the combined extracts washed with water and dried (MgSO$_4$). Solvent was evaporated at reduced pressure and the residue vacuum-distilled to give 4-(4-dimethylaminomethyl-2-pyridylmethylthio)butyronitrile (7.16 g) as a pale yellow liquid, b.p.$_{0.01\ mm}$170° C.

(c) 4-(4-Dimethylaminomethyl-2-pyridylmethylthio)butyronitrile (7.11 g) was dissolved in a mixture of dry methanol (35 ml) and dry chloroform (70 ml) and the stirred solution cooled to −4° C. under nitrogen. Dry hydrogen chloride gas was passed through the solution for 2.25 hours, keeping the temperature below 0° C. After having been allowed to stand in a stoppered flask for 20 hours at ca. 4° C., the solution was added to a solution of potassium carbonate (27 g) in ice-water (400 ml). The chloroform layer was separated off and the aqueous layer extracted with chloroform (3×80 ml). The combined extracts were dried (K$_2$CO$_3$) and chloroform evaporated at reduced pressure to give methyl 4-(4-dimethylaminomethyl-2-pyridylmethylthio)butyronimidate (6.96 g) as a yellow oil.

(d) Methyl 4-(4-dimethylaminomethyl-2-pyridylmethylthio)butyronimidate (6.96 g), ammonium chloride (1.32 g) and ethanol (45 ml) were stirred at room temperature for 4.5 hours. Ethanol was evaporated at reduced pressure and the residue chromatographed using silica gel and a chloroform-methanol gradient elution. Fractions containing the required product (as shown by TLC) were combined and solvent evaporated at reduced pressure to give 4-(4-dimethylaminomethyl-2-pyridylmethylthio)butyronamidine hydrochloride (4.67 g).

(e) A solution of 4-(4-dimethylaminomethyl-2pyridylmethylthio)butyronamidine hydrochloride (2.32 g) in methanol (25 ml) was added to a solution of sodium (0.40 g) in methanol (15 ml). The mixture was refluxed for 0.5 hour and ethyl 2-formyl-3-(6-methyl-3-pyridyl)propionate (1.69 g) added portionwise over 15 minutes. The mixture was refluxed for 21 hours and the methanol was evaporated at reduced pressure. The residue was dissolved in water (25 ml) and the solution was washed with ether (3×20 ml) and adjusted to pH 9 with glacial acetic acid. A tacky oil precipitated and this gradually formed a white solid. The solid was filtered off, washed with water and recrystallised from isopropanol-ether to give 2-[3-(4-dimethylaminomethyl-2-pyridylmethylthio)propyl]-5-(6-methyl-3-pyridylmethyl)-4-pyrimidone (1.39 g), m.p. 110°–111.5° C.

Example 7

(a) To a solution of S-(4-dimethylaminomethyl-2pyridylmethyl)isothiourea trihydrochloride (21.54 g) and 3-chloropropionitrile (8.01 g) in water (90 ml) and ethanol (65 ml) at 0° C (ice-salt bath) under nitrogen, was added dropwise over 30 minutes, a solution of sodium hydroxide (11.5 g) in water (120 ml), keeping the temperature below 3° C. After having been stirred for 7 hours and allowed to stand for 20 hours, the solution was extracted with 3:1 chloroform:ethanol (3×160 ml). The combined extracts were washed with water and dried (MgSO$_4$) Solvent was evaporated at reduced pressure and the residue vacuum-distilled to give 3-(4-dimethylaminomethy-2-pyridyl-methylthio)propionitrile (13.66 g) as a pale yellow liquid, b.p.$_{0.005\ mm}$148°–152° C.

(b) 3-(4-Dimethylaminomethyl-2-pyridylmethylthio)propionitrile (13.60 g) was dissolved in a mixture of dry methanol (70 ml) and dry chloroform (140 ml) and the stirred solution cooled to −5° C. under nitrogen. Dry hydrogen chloride gas was passed through the solution for 3.75 hours, keeping the temperature below 0° C. The solution was allowed to stand in a stoppered flask at ca. 4° C. for 24 hours and was added to a solution of potassium carbonate (45 g) in ice-water (500 ml). The chloroform layer was separated off and the aqueous layer extracted with chloroform (3×150 ml). The combined extracts were dried ($K_2CO_3$ and chloroform evaporated at reduced pressure to give methyl 3-(4-dimethylaminomethyl-2-pyridylmethylthio)propionimidate (14.02 g) as an oil.

(c) Methyl 3-(4-dimethylaminomethyl-2-pyridylmethylthio)propionimidate (8.68 g), ammonium chloride (1.74 g) and ethanol (60 ml) were stirred at room temperature for 4 hours. Ethanol was evaporated at reduced pressure and the residue chromatographed using silica gel and a chloroform-methanol gradient elution. Fractions containing the required product (as shown by TLC) were combined and solvent evaporated at reduced pressure to give 3-(4-dimethylaminomethyl-2-pyridylmethylthio)propionamidine hydrochloride (2.30 g).

(d) A solution of 3-(4-dimethylaminomethyl-2pyridylmethylthio)propionamidine hydrochloride (2.27 g) in methanol (25 ml) was added to a solution of sodium (0.45 g) in methanol (20 ml). The mixture was refluxed for 30 minutes and ethyl 2-formyl-3-(6-methyl-3-pyridyl)propionate (1.74 g) was added portionwise over 10 minutes. This mixture was refluxed for 24 hours and the methanol evaporated at reduced pressure. The residue was dissolved in water (30 ml), the solution washed with ether (3×25 ml) and adjusted to pH 9 with glacial acetic acid, whereupon a tacky oil precipitated. This was extracted with chloroform (3×30 ml) and the combined extracts were dried ($MgSO_4$) and evaporated to dryness at reduced pressure. The residue was recrystallised from isopropanol-ether to give 2-[2-(4-dimethylaminomethyl-2-pyridylmethylthio)methyl]-5-(6-methyl-3-pyridylmethyl)-4-pyrimidone (1.06 g), m.p. 117-8° C.

Example 8

(a) A solution of 3-(1-piperidinylmethyl)phenol (12.05 g) in dry tetrahydrofuran (50 ml) was added dropwise to a suspension of sodium hydride [from 6.0 g of 50% suspension in oil washed with petroleum ether] in dry tetrahydrofuran (70 ml). The mixture was stirred under reflux for 30 minutes and allowed to cool. 4-Bromobutyronitrile (14.89 g, 10.0 ml) was added to the cool mixture and the mixture so obtained was stirred under reflux for 22 hours. Tetrahydrofuran was evaporated under reduced pressure and the residue was dissolved in water (100 ml). The solution was extracted with ether (3×50 ml), and the aqueous layer was adjusted to pH 9 with $K_2CO_3$. The aqueous solution was extracted with chloroform (3×100 ml), the chloroform extracts were dried ($K_2CO_3$ and chloroform was removed under reduced pressure to give a pale brown oil, (16.22 g). This oil was purified by column chromatography (Kieselgel 60 70–230 mesh silica) using chloroform as eluant. The fractions containing the desired product were collected and the solvent was evaporated in vacuo to give 4-[3-(1-piperidinylmethyl)phenoxy]butyronitrile as an oil (11.37 g).

(b) Dry hydrogen chloride gas was introduced into a stirring solution of 4-[3-(1-piperidinylmethyl)phenoxy]butyronitrile (15.62 g) in dry methanol (65 ml) and dry chloroform (130 ml) cooled to −5° C. (ice-salt bath) under nitrogen over 1.75 hours at a rate such that the temperature did not exceed 1° C. The solution was stirred at 0° C. for a further hour, and left to stand (at ca. 4° C.) for ca. 16 hours. The mixture was poured on to a solution of potassium carbonate (45 g) in ice-water (ca. 500 ml). The organic layer was separated off and the aqueous layer extracted with chloroform (4×150 ml). The combined organic layers were dried ($K_2CO_3$) and evaporated in vacuo to give methyl 4-[3-(1-piperidinylmethyl)phenoxy]butyronimidate (14.46 g) as an oil.

(c) Methyl 4-[3-(1-piperidinylmethyl)phenoxy]butyronimidate (14.46 g), ammonium chloride (2.66 g) and ethanol (100 ml) were stirred at room temperature for 5 hours and allowed to stand (ca. 16 hours). Ethanol was removed under reduced pressure and the residue purified using medium pressure chromatography, with Kieselgel 60 silica 70–230 mesh (pre-column) and 230–400 mesh (main column) and a chloroform methanol gradient elution. The fraction containing the desired product (9:1 chloroform:methanol) were collected and the solvent was evaporated in vacuo to give 4-[3-(1-piperidinylmethyl)phenoxy]butyronamidine hydrochloride (8.03 g) as a glassy solid.

(d) A solution of 4-[3-(1-piperidinylmethyl)phenoxy]butyronamidine hydrochloride (1.09 g) in methanol (10 ml) was added to a solution of sodium (0.20 g) in methanol (10 ml). The mixture was refluxed for 30 minutes, and ethyl α-formyl-β-(6-methylpyrid-3-yl)propionate (0.77 g) added, and the mixture refluxed for 48 hours. Methanol was removed under reduced pressure and the residue dissolved in water (20 ml). The solution was extracted with ether (3×15 ml), and carefully adjusted with glacial acetic acid to pH 9. A white solid precipitated out and was filtered off, washed with water and recrystallised from isopropanol-ether to give 2-[[3-[3-(1-piperidinylmethyl)phenoxy]propyl]]-5-(6-methyl-3-pyridylmethyl)-4-pyrimidone (0.64 g) as a white solid, m.p. 137°-8° C.

Example 9

A solution of 4-[3-(1-piperidinylmethyl)phenoxy]butyronamidine hydrochloride (2.80 g) in methanol (15 ml) was added to a solution of sodium (0.55 g) in methanol (20 ml). The mixture was stirred under reflux for 30 minutes, to this was added a solution of ethyl α-formyl-β-(2-methoxy-4-pyridyl)propionate (2.13 g) in methanol (15 ml). The mixture was stirred under reflux for 19 hours. Methanol was removed under reduced pressure and the residue was dissolved in water (40 ml). The solution was adjusted with acetic acid to pH 9 and an oil precipitated. The aqueous layer was extracted with chloroform (3–50 ml). The combined extracts were dried ($MgSO_4$) and the chloroform was evaporated under reduced pressure. The residue was purified by column chromatography using Kieselgel 60 silica 70–230 mesh and a chloroform-methanol gradient elution. Fractions containing the required product (19:1 chloroform:methanol) were evaporated in vacuo, and the residue was recrystallised from ether to give 2-[[3-[3-(1-piperidinylmethyl)phenoxy]propyl]]-5-(2-methoxy-4-pyridylmethyl)-4pyrimidone as a white solid (0.66 g), m.p. 93°-4° C.

Example 10

2-[[3-[3-(1-Piperidinylmethyl)phenoxy]propyl]]-5-(2-methoxy-4-pyridylmethyl)-4-pyrimidone (0.49 g) was dissolved in ethanolic hydrogen chloride (5 ml) and ethanol (25 ml) and the solution refluxed for 45 hours. Solvent was evaporated off under reduced pressure and the residue dissolved in water (25 ml). The solution was adjusted to pH 11 with potassium carbonate solution, whereupon an oily solid precipitated This was extracted with chloroform (3×20 ml) and the combined extracts dried (MgSO4) and chloroform evaporated in vacuo. The residue was recrystallised from isopropanol-ether to give 2-[[3-[3-(1-piperidinylmethyl)phenoxy]propyl]]-5-(2-hydroxy-4-pyridylmethyl)-4-pyrimidone as a white solid (0.39 g), m.p. 167°-9° C.

What is claimed is:

1. A compound of formula (I):

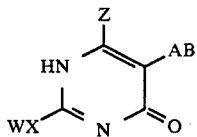

or a pharmaceutically acceptable salt thereof, where

W is 2-furanyl or 2-thienyl optionally substituted in the 5-position with $R^1R^2N(CH_2)_a$—; 2-pyridyl optionally substituted in the 4- or 6- position with $R^1R^2N(CH_2)_a$—; phenyl substituted in the 3- or 4-position with $R^1R^2N(CH_2)_a$—; 4-imidazolyl optionally substituted in the 5-position with methyl or bromine; 2-pyridyl optionally substituted in the 3-position with $C_{1-4}$ alkyl, $C_{1-4}$ alkoxy, halogen, amino or hydroxy; 2-thiazolyl or 2-guanidino-4-thiazolyl;

X is $(CH_2)_b$ in which b is from 3 to 6, or $(CH_2)_dS(CH_2)_e$ in which d and e are the same or different and are from 1 to 3 or, when W is substituted phenyl, or 2-pyridyl substituted in the 4- or 6-position with $R^1R^2N(CH_2)_a$—, $O(CH_2)_f$ in which f is from 2 5 and $(CH_2)_f$ is attached to the pyrimidone ring;

Z is hydrogen or $C_{1-4}$ alkyl;

A is $C_1-C_5$ alkylene or $(CH_2)_pA^1)(CH_2)_q$—where $A^1$ is oxygen or sulphur and p and q are such that their sum is from 1 to 4;

B is pyridyl optionally substituted with one or more $C_{1-4}$ alkyl, or $C_{1-4}$ alkoxy or hydroxy groups or halogen atoms or with N-oxo or phenyl optionally substituted with one or more $C_{1-4}$ alkyl or Chd 1-4 alkoxy groups or halogen atoms or B is 6-(2,3-dihydro-1,4-benzodioxinyl) or 5-(1,3-benzodioxolyl) or B is 2-furanyl or 2-thienyl optionally substituted in the 5-position with $R^1R^2N(CH_2)_a$—; phenyl substituted in the 3- or 4-position with $R^1R^2N(CH_2)_a$— or 3-pyridyl substituted in the 5- or 6- position or 4-pyridyl substituted in the 2-position by $R^1R^2N(CH_2)_a$—;

$R^1$ and $R^2$ can be the same or different and are hydrogen or $C_{1-4}$ alkyl or together form 1,4-butanediyl, 1,5-pentanediyl, 1,6-hexanediyl or 1,7-heptanediyl; and a is 1 to 4.

2. A compound according to claim 1, where W is 2-furanyl or 2-thienyl optionally substituted in the 5-position with $R^2R^2N(CH_2)_a$—; 4-imidazolyl optionally substituted in the 5-position with methyl or bromine; or 2-pyridyl substituted in the 4-position with $R^1R^2N(CH)_a$; or phenyl substituted in the 3position with $R^1R^2N(CH)_a$— or 2-pyridyl optionally substituted in the 3-position with $C_{1-4}$alkyl, $C_{1-4}$ alkoxy, halogen, amino or hydroxy; 2-thiazolyl or 2-guanidino-4-thiazolyl.

3. A compound according to claim 2, where W is 2-furanyl or 2-thienyl substituted in the 5-position or 2-pyridyl substituted in the 4-position or phenyl substituted in the 3-position with $R^1R^2N(CH_2)_a$—; or is 2-guanidino-4-thiazolyl.

4. A compound according to claim 3, where W is 2-furanyl or 2-thienyl substituted in the 5-position with $R^1R^2N(CH_2)_a$— in which $R^1$ and $R^2$ are both methyl and a is 1.

5. A compound according to claim 4, where W is 5-dimethylaminomethyl-2-furanyl.

6. A compound according to claim 3, where W is 2 pyridyl substituted in the 4-position with $R^1R^2N(CH_2)_a$— in which $R^1$ and $R^2$ are both methyl or together represent a 1,5-pentanediyl group and a is 1.

7. A compound according to claim 6 where W is 4-(1-piperidinylmethyl)pyrid-2-yl.

8. A compound according to claim 3, where W is phenyl substituted in the 3-position with $R^1R^2N(CH_2)_a$—, in which $R^1$ and $R^2$ are both methyl or together represent a 1,5-pentanediyl group and a is 1.

9. A compound according to claim 8 where W is 3-(1-piperidinylmethyl)phenyl.

10. A compound according to claim 1, where WX is W—$CH_2SCH_2CH_2$ or W—$OCH_2CH_2CH_2$.

11. A compound according to claim 1, where Z is hydrogen.

12. A compound according to claim 1, where A is $CH_2$.

13. A compound according to claim 1, where B is 2,3-dihydro-1,4-benzodioxinyl) or 5-(1,3-benzodioxolyl) or 2-pyridyl, 3-pyridyl, 4-pyridyl, which pyridyl rings are optionally substituted with one or more $C_{1-4}$ alkyl or $C_{1-4}$ alkoxy groups, or pyridyl substituted by hydroxy, or 2-furanyl or 2-thienyl substituted in the 5-position or 3-pyridyl substituted in the 6-position or 4-pyridyl substituted in the 2-position with $R^1R^2N(CH_2)_a$—.

14. A compound according to claim 13, where B is 3-pyridyl, 6-methyl-3-pyridyl, 5,6-dimethyl-3-pyridyl, 6-methoxy-3-pyridyl, 2-methoxy-4-pyridyl, 6-hydroxy-3pyridyl, 2-hydroxy-4-pyridyl, 5-dimethylaminomethyl-2furanyl, or 6-dimethylaminomethyl-3-pyridyl.

15. A compound according to claim 14, where B is 6-methyl-3-pyridyl.

16. A compound according to claim 14 where B is 2-hydroxy-4-pyridyl.

17. A compound according to claim 1, which is selected from 2-[2-(2-guanidino-4-thiazolylmethylthio)ethyl]-5-(6-methyl-3-pyridylmethyl)-4-pyrimidone or a pharmaceutically acceptable salt thereof.

18. A compound according to claim 1, which is selected from 2-[2-(2-dimethylaminomethyl-5-furanyl methylthio)-ethyl]-5-(6-methyl-3-pyridylmethyl)-4pyrimidone or a pharmaceutically acceptable salt thereof.

19. A compound according to claim 1, which is selected from 2-[3-(5-methyl-4-imidazolylmethylthio)-propyl]-5-(6-methyl-3-pyridylmethyl)-4-pyrimidone or a pharmaceutically acceptable salt thereof.

20. A compound according to claim 1, which is selected from 2-[3-(5-dimethylaminomethyl-2-furanylmethylthio)propyl]-5-(6-methyl-3-pyridylmethyl)-4-pyrimidone or a pharmaceutically acceptable salt thereof.

21. A compound according to claim 1, which is selected from 2-[[3-[4-(1-piperidinylmethyl)-2-pyridyloxy]]-5-(6-methyl-3-pyridylmethyl)-4-pyrimidone or a pharmaceutically acceptable salt thereof.

22. A compound according to claim 1, which is selected from 2-[3-(4-dimethylaminomethyl-2-pyridylmethylthio)propyl]-5-(6-methyl-3-pyridylmethyl)-4-pyrimidone or a pharmaceutically acceptable salt thereof.

23. A compound according to claim 1, which is selected from 2-[2-(4-dimethylaminomethyl-2-pyridylmethylthio)ethyl]-5-(6-methyl-3-pyridylmethyl)-4-pyrimidone or a pharmaceutically acceptable salt thereof.

24. A compound according to claim 1, which is selected from 2-[3-[3-(1-piperidinylmethyl)-2-phenyloxy]propyl]-5-(6-methyl-3-pyridylmethyl)-4-pyrimidone or a pharmaceutically acceptable salt thereof.

25. A compound according to claim 1, which is selected from 2-[3-[3-(1-piperidinylmethyl)-2-phenyloxy]propyl]-5-(2-methoxy-4-pyridylmethyl)-4-pyrimidone or a pharmaceutically acceptable salt thereof.

26. A compound according to claim 1, which is selected from 2-[3-[3-(1-piperidinylmethyl)-2-phenyloxy]propyl]-5-(2-hydroxy-4-pyridylmethyl)-4-pyrimidone or a pharmaceutically acceptable salt thereof.

27. A hydrochloric, hydrobromic, sulphuric, phosphoric, acetic, citric or maleic acid salt of a compound of formula (I) according to claim 1.

28. A pharmaceutical composition having histamine $H_2$-antagonist activity comprising an effective amount of a compound according to claim 1 and a pharmaceutically acceptable carrier.

29. A method of blocking histamine $H_2$-receptors which comprises administering to an animal an effective amount of a compound according to claim 1.

* * * * *

UNITED STATES PATENT AND TRADEMARK OFFICE
CERTIFICATE OF CORRECTION

PATENT NO. : 4,808,589

DATED : February 28, 1989

INVENTOR(S) : Thomas H. Brown

It is certified that error appears in the above-identified patent and that said Letters Patent is hereby corrected as shown below:

Column 2, line 44: "3-pyridyl" should be -- 4-pyridyl -- ;

Column 3, line 50: "2-pyridyl" should be -- 3-pyridyl -- ;

Column 4, line 12: "(6-methyl-3-pyridylmethyl)-4-pyrimidone" should be -- (2-methoxy-4-pyridylmethyl)-4-pyrimidone -- ;

Column 4, line 14: "(2-methoxy-4-" should be -- (2-hydroxy-4- -- ;

Column 4, line 15: delete entire line "hydroxy-4-pyridylmethyl)-4-pyrimidone" ;

Column 9, line 54: at end of line "2-[2-(2-" should be -- 2-[2- -- ;

Claim 1, column 17, line 39: "is from 2 5" should read -- is from 2 to 5 -- ;

UNITED STATES PATENT AND TRADEMARK OFFICE
CERTIFICATE OF CORRECTION

PATENT NO. : 4,808,589

DATED : February 28, 1989

INVENTOR(S) : Thomas H. Brown

It is certified that error appears in the above-identified patent and that said Letters Patent is hereby corrected as shown below:

Claim 1, column 17, line 48:

at end of line "Chd 1-4" should be -- $C_{1-4}$ -- ;

Claim 2, column 17, line 63:

"$R^2R^2N(CH_2)_a$-" should be -- $R^1R^2N(CH_2)_a$- -- ;

Claim 2, column 17, lines 65-66:

"$R^1R^2N(CH)_a$;" should be -- $R^1R^2N(CH_2)_a$; -- ;

Claim 2, column 17, line 67:

"$R^1R^2N(CH)_a$-" should be -- $R^1R^2N(CH_2)_a$- -- ;

Claim 13, column 18, line 34:

"2,3-dihydro-" should be -- 6-(2,3-dihydro- -- ;

Claim 21, column 19, line 1: "y]]-5-(6-methyl-3-pyridylmethyl)-" should be
-- y]propyl]]-5-(6-methyl-3-pyridylmethyl) -- ;

UNITED STATES PATENT AND TRADEMARK OFFICE
CERTIFICATE OF CORRECTION

PATENT NO. : 4,808,589

DATED : February 28, 1989

INVENTOR(S) : Thomas H. Brown

It is certified that error appears in the above-identified patent and that said Letters Patent is hereby corrected as shown below:

Claim 21, column 19, line 1: "y]]-5-(6-methyl-3-pyridylmethyl)-" should be --y]propyl]]-5-(6-methyl-3-pyridylmethyl) --;

Signed and Sealed this

Twenty-sixth Day of June, 1990

Attest:

HARRY F. MANBECK, JR.

Attesting Officer

Commissioner of Patents and Trademarks